United States Patent [19]
Weithmann et al.

[11] Patent Number: 5,547,971
[45] Date of Patent: Aug. 20, 1996

[54] USE OF LEFLUNOMIDE FOR INHIBITING INTERLEUKIN 8

[75] Inventors: Klaus U. Weithmann, Hofheim; Robert R. Bartlett, Darmstadt, both of Germany

[73] Assignee: Hoechst Aktiengesellschaft, Frankfurt am Main, Germany

[21] Appl. No.: 411,848

[22] Filed: Mar. 28, 1995

Related U.S. Application Data

[63] Continuation of Ser. No. 177,980, Jan. 6, 1994, abandoned.

[30] Foreign Application Priority Data

Jan. 8, 1993 [DE] Germany .......................... 43 00 278.1

[51] Int. Cl.⁶ .................................................. A61K 31/42
[52] U.S. Cl. .............................................................. 514/378
[58] Field of Search .............................................. 514/378

[56] References Cited

U.S. PATENT DOCUMENTS

| | | | |
|---|---|---|---|
| 4,351,841 | 9/1982 | Kammerer et al. | 514/378 |
| 4,965,276 | 10/1990 | Bartlett et al. | 514/378 |

OTHER PUBLICATIONS

Peveri et al., "A Novel Neutrophil–Activating Factor Produced By Human Mononuclear Phagocytes", J. Exp. Med., 167:1547–1559 (1988).
Djeu et al, "Functional Activation of Human Neutrophils By Recombinant Monocyte–Derived Neutrophil Chemotactic Factor/IL–8", J. Immunol., 144(6):2205–2210 (1990).
Bartlett et al., "Leflunomide (HWA 486), A Novel Immunomodulating Compound For The Treatment Of Autoimmune Disorders And Reactions Leading To Transplantation Rejection", Agents and Actions, 32:10–21 (1991).
Furuta et al., "Production and Characterization of Recombinant Human Neutrophil Chemotactic Factor", J. Biochem., 106:436–441 1989.
Van Damme et al., "A Novel NH₂–Terminal Sequence––Characterized Human Monokine Possessing Neutrophil Chemotactic, Skin–Reactive, And Granulocytosis–Promoting Activity", J. Exp. Med., 167:1364–1376 (1988).
Elford et al., "Induction Of Neutrophil–Mediated Cartilage Degradation By Interleukin–8", Arthritis and Rheumatism, 34(3): 325–332 (1991).
Farina et al., "Monocyte–Derived Neutrophil Chemotactic Factor (MDNCF): A Stimulator Of Neutrophil Function", Faseb J., 3:1333 (1989).
Larsen et al., "The Neutrophil–Activating Protein (NAP–1) Is Also Chematic For T Lymphocytes", Science, 243:1464–1466 (1989).
Axton et al., "Novel Immunosuppressive Butenamides", J. Chem. Soc. Perkin Trans. 1:2203–2213 (1992).
Yoshimura et al., "Neutrophil Chemotactic Factor Produced By Lipopolysaccharide (LPS)–Stimulated Human Blood Mononuclear Leukocytes: Partial Characterization and Separation From Interleukin 1 (IL 1)", J. Immunol., 139(3):788–793 (1987).
Schroder et al., "Purification and Partial Biochemical Charactrization Of A Human Monocyte–Derived, Neutrophil–Activating Peptide That Lacks Interleukin 1 Activity", J. Immmunol., 139(10):3474–3483 (1987).
T. T. Glant et al., "Immunomodulation of Proteoglycan–Induced . . .", Immunopharmacology, 23:105–116 (1992).

*Primary Examiner*—Jerome D. Goldberg
*Attorney, Agent, or Firm*—Finnegan, Henderson, Farabow, Garrett & Dunner, L.L.P.

[57] ABSTRACT

The use of leflunomide for inhibiting interleukin 8 N-(4-Trifluoromethylphenyl)-5-methylisoxazole-4-carboxamide is an effective compound for preventing and treating disorders in which interleukin 8 is involved. It is used as a pharmaceutical.

1 Claim, No Drawings

USE OF LEFLUNOMIDE FOR INHIBITING INTERLEUKIN 8

This application is a continuation, of application Ser. No. 08/117,980, filed Jan. 6, 1994, now abandoned.

Leflunomide (see formula, N-(4-trifluoromethylphenyl)-5-methylisoxazole-4-carboxamide) is already known as a chemical compound (EP 0013376, EP 0217206, U.S. Pat. Nos. 4,351,841, 4,965,276).

In addition to its antiinflammatory effects, which have already been disclosed, this substance also brings about immunomodulatory effects which qualify it for use in the treatment of autoimmune diseases and transplant rejection reactions. It is also already known that a metabolite with the designation N-(4-trifluoromethylphenyl)-2-cyano-3-hydroxycrotonamide (see formula) is responsible for the therapeutic effects of leflunomide.

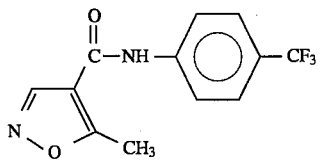

Leflunomide

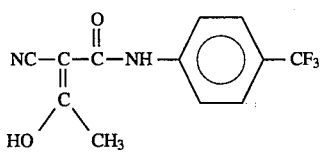

Leflunomide metabolite

In correspondence with this finding, the pharmacological effects of leflunomide cited above can also be obtained by administering this said metabolite (Bartlett et al., Agents and Actions, 32 (1991) 10–21).

Axton et al., J. Chem. Soc. Perkin Trans. 1 (1992) 2203 ff. also describe how leflunomide does not represent the active principle and that, instead, this primary metabolite exhibits the biological effects.

It has been possible to demonstrate both in the literature (Bartlett et al., Agents and Actions, 32 (1991) 10–21) and in our own experiments that the therapeutic effects described in more detail below cannot be obtained by administering the leflunomide metabolite. Thus, it was found, in accordance with the invention, that leflunomide exerts a strong inhibitory effect on the synthesis and liberation of cytokines from human blood cells, whereas the leflunomide metabolite does not exhibit this advantageous effect.

Under the experimental conditions employed in accordance with the invention, no appreciable metabolism of leflunomide takes place, and the inhibitory effect is to be ascribed exclusively to the substance leflunomide.

The cytokines are a class of diverse, biologically highly potent, peptides whose structures are already known. It is likewise already known that they are induced and synthesized endogenously as transmitter substances.

The suppression of cytokines in the human or animal body is of great medical importance since excessive levels of these cytokines can lead to the occurrence or outbreak of numerous disorders.

Such disorders could be treated with a medicament which inhibits the undesirable effect of the cytokine, which might already be present, on the organ, cell, tissue and receptor systems of the body; however, it is now a further, significant advantage of the present invention that the use of leflunomide inhibits the actual synthesis and liberation of the cytokine so that the latter never even comes into being and the emergence of the disorder can thus be prevented at a very early phase.

The present invention relates to the use of leflunomide for preparing a pharmaceutical for preventing and treating disorders of the human and animal body in which the cytokine with the designation interleukin 8 (IL-8) is involved.

The present invention further relates to the use of leflunomide for treating such disorders.

The invention also relates to pharmaceuticals which contain an effective quantity of leflunomide in addition to pharmaceutically suitable and physiologically tolerated excipients, diluents and/or other active compounds and auxiliary substances.

The invention also relates to a process for preparing a pharmaceutical for preventing and treating disorders in which interleukin 8 is involved, wherein leflunomide is brought into a suitable preparation form together with pharmaceutically suitable and physiologically acceptable excipients and, where appropriate, further suitable active compounds, additives or auxiliary substances.

IL-8 and its disease-causing effects are described in detail in Ibelgaufts, Lexikon Zytokine (Cytokine Dictionary), Medikon Verlag, Munich 1992, and in the literature cited therein.

On account of its diverse biological effects, IL-8 is known as neutrophil chemotaxis factor (NCF) or granulocyte chemotaxis peptide (GCP), or else neutrophil activating factor (NAF) or T-cell chemotactic factor (TCF). The diverse biological effects of IL-8 are also described in detail in, for example, Yoshimura et al., J. Immunol. 139 (1987) 788, Larsen et al., Science 243 (1989) 1464, Schroeder et al., J. Immunol. 139 (1987) 3474, Peveri et al., J. Exp. Med. 167 (1988) 1547, Dieu et al., J. Immunol. 144 (1990) 2205, Farina et al., Faseb J. 3 (1989) A1333, Furuta et al., J. Biochem. 106 (1989) 436, as well as in Van Damme et al., J. Exp. Med. 167 (1988) 1364. Thus, this cytokine has a broad spectrum of activity as an inducer of chemotaxis and the liberation of superoxide anions and lysosomal enzymes in neutrophil systems. IL-8 also stimulates the chemotactic activity of basophils and T lymphocytes, while inhibiting the adhesion of leucocytes to endothelial cells. Intraperitoneal injection of IL-8 leads to neutrophilia. Il-8activated white blood cells are able to migrate from the synovium right into the cartilage cells and there play a leading role in the genesis of arthritis. It should also be emphasized that IL-8 can be detected in the blood even in the initial phase of acute injuries, and also, in particular, even following relatively minor damage to the skin. In addition to this, it has a mitogenic effect on epidermal cells and can, as a consequence, give rise to skin cancer.

It is evident, therefore, that IL-8, in particular, occupies a central position as the trigger for various disorders and symptoms of disorders. Wounds which do not readily heal, arthritis and skin cancer are predominantly serious disorders which can currently either not be treated at all or only treated inadequately. For this reason too, the effect of leflunomide which has been discovered is of great importance.

The present invention furthermore relates to the use of leflunomide for preventing and treating disorders such as cartilage destruction, wounds which do not readily heal or skin cancer (Elford and Cooper, Arthritis and Rheumatism, 34 (1991) page 325).

Pharmaceutical forms and pharmaceutical preparations of leflunomide, which have been prepared in the customary manner, can also, in particular, be used for treating these disorders.

Suitable solid or liquid pharmaceutical preparation forms are, for example, granules, powders, coated tablets, tablets, (micro)capsules, suppositories, syrups, juices, suspensions, emulsions, drops or injectable solutions, as well as preparations having a protracted release of active compound, in whose preparation customary adjuvants, such as excipients, disintegrants, binding agents, coating agents, swelling agents, gildants, lubricants, flavorants, sweeteners or solubilizers are used. Frequently used auxiliary substances which may be mentioned are, for example, magnesium carbonate, titanium dioxide, lactose, mannitol and other sugars, talc, milk protein, gelatin, starch, cellulose and its derivatives, animal and plant oils, polyethylene glycols, and solvents, such as, for example, sterile water and monohydric or polyhydric alcohols, e.g. glycerol.

In human medicine, dose units of 3 to 5 mg, preferably 10, 25 or 50 mg, per patient (70 kg body weight) are administered. If required medically, the dose unit can be increased to 100, 200 or 500 mg per patient. Dosing can take place once daily to once weekly, preferably up to three or four times daily. Administration can be effected orally, peritoneally, intravenously, intraarticularly or transdermally in a customary manner. The corresponding doses to be administered within veterinary medicine can also be readily calculated from these data.

Finally, in the preparation of the abovementioned pharmaceutical preparation forms, leflunomide can also be formulated together with other suitable active compounds, for example antiuricopathic agents, blood plateletaggregation inhibitors, analgesics, and other steroidal or non-steroidal antiinflammatory agents.

It was possible to demonstrate the effects of leflunomide experimentally on an isolated blood cell fraction (mononuclear cells), which cell fraction did not, to any appreciable extent, metabolize the leflunomide to its metabolites.

EXAMPLE 1

The mononuclear cells from freshly isolated human citrate blood were enriched in accordance with known standard procedures (see Tiku et al., J. Immunol. 136/10 (1986) 3677):

10 ml of freshly prepared human citrate blood were carefully underlaid with 15 ml of Lymphoprep$^{(R)}$ (Molter GmbH, Heidelberg) and then centrifuged at 400 ×g for 40 min. at 20° C. The cell fraction which was visible as a white ring at the phase boundary was removed with the aid of a syringe, diluted 1:1 (v/v) with PM-16 buffer (from Serva Feinbiochemica GmbH & Co. KG, Heidelberg) and then centrifuged, as above, for 10 min. The supernatant was washed with 10 ml of RPMI 1640 buffer (Gibco, Berlin) to which 300 mg/l L-glutamine had previously been added. The washed cell fraction was taken up in 1 ml of RPMI 1640 to which 300 mg/l L-glutemine, 25 mmol/l HEPES (Gibco, Berlin), 0.1 g/ml streptomycin and 0.1 g/ml penicillin had previously been added. Using a cell counter (type IT, from Coulter Diagnostics, Krefeld), the cell suspension, which is composed of about 90% lymphocytes and 10% monocytes, was adjusted to about 5 million cells/ml. Cell viability was monitored before and after the inhibition experiments using the known lactate dehydrogenase method. In this case, no change in viability was observed.

The synthesis and liberation of cellular IL-8 was induced by adding a solution of 500 ng of lipopolysaccharide (Salmonella abortus equi, Sigma GmbH, Deisenhofen) in 0.01 ml of dimethyl sulfoxide/water (1:10, v/v) to 0.48 ml of the above-described cell fraction. At the same time, a solution of leflunomide or leflunomide metabolite in 0.01 ml of dimethyl sulfoxide (for the final concentration in each case, see Tab. 1) was added to the cell fraction and the mixture was left at 37° C. for 1h in a commercially available incubator. After cooling down to 0° C., the samples were centrifuged for 1 min. in a bench centrifuge and in each case 0.025 ml aliquots of the supernatant were examined for their TNFalpha content using a "sandwich" enzyme immuno test kit (from Biermann GmbH, Bad Nauheim) in accordance with the manufacturer's instructions. The control values were determined without the addition of leflunomide or its metabolites and set at 100%. In particular, any possible influence of dimethyl sulfoxide on the TNFalpha level was excluded by appropriate comparative measurements.

In addition, aliquots of the test sample containing leflunomide were removed in a time-dependent manner and tested for their content of leflunomide or leflunomide metabolite using high pressure liquid chromatography (C-18 column 3.9×150 mm, Waters GmbH, Eschborn, FRG, eluent: 600 ml of methanol/350 ml of water/50 ml of tetrahydrofuran/1 ml of phosphoric acid; flow rate 0.7 ml/min. at 2000 pounds per square inch (psi); detection in the ultraviolet range at 273 nm). It was found that, under the conditions employed, leflunomide is only very slowly, with a half life of about 10 hours, metabolized to its metabolites.

TABLE 1

| Substance under examination | Concentration mmol/l | IL-8 in the supernatant % +/− standard deviation | Number of experiments n = |
|---|---|---|---|
| Leflunomide metabolite | 0.1 | 99 | 2 |
| | 0.05 | 97 | 2 |
| Leflunomide | 0.1 | 61 +/− 11 | 3 |
| | 0.05 | 83 | 2 |
| Without either | 0 | 100 | |

The experiments in Tab. 1 demonstrate that the leflunomide metabolite has practically no effect on the IL-8 level, whereas the IL-8 level is clearly lowered following the addition of leflunomide.

EXAMPLE 2

Preparation of N-(4-trifluoromethylphenyl)-5-methylisoxazole-4-carboxamide

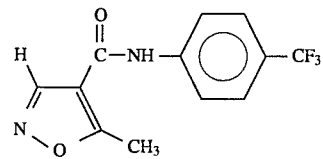

A solution of 0.05 mol of 5-methylisoxazole-4-carbonyl chloride (7.3 g) in 20 ml of acetonitrile is added dropwise, at room temperature, to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile on each occasion, and the combined filtrates are concentrated under reduced pressure. Yield: 12.8 g of white, crystalline N-(4-trifluoromethylphenyl)-5-methylisoxazole-4 -carboxamide (leflunomide).

EXAMPLE 3

Acute toxicity following intraperitoneal administration

The acute toxicity following intraperitoneal administration of the test substance was carried out using NMRI mice (20 to 25 g) and SD rats (120 to 195 g). The test substance was suspended in a 1% strength solution of sodium carboxmethyl cellulose. The different doses of the test substance were administered to the mice in a volume of 10 ml/kg of body weight and to the rats in a volume of 5 ml/kg of body weight. 10 animals were used per dose. After 3 weeks, the acute toxicity was determined by the method of Litchfield and Wilcoxon. The results are summarized in Table 2.

TABLE 2

|  | Leflunomide acute toxicity intraperitoneally $LD_{50}$ (mg/kg) |
| --- | --- |
| NMRI mouse | 185 (163–210) |
| SD rat | 170 (153–189) |

We claim:

1. A method for the treatment of a condition characterized by the elevated interleukin 8 level in a human or animal suffering from skin cancer or wounds that do not readily heal, wherein the method comprises administering to said human or animal N-(4-trifluoromethylphenyl)-5-methyl-isoxazole-4-carboxamide in an amount sufficient to inhibit the synthesis and liberation of said interleukin.

* * * * *